US012188156B2

(12) United States Patent
Tejeda-Alejandre et al.

(10) Patent No.: US 12,188,156 B2
(45) Date of Patent: Jan. 7, 2025

(54) THREE DIMENSIONAL PRINTING MODALITY COMBINING FUSED DEPOSITION MODELING AND ELECTROSPINNING

(71) Applicants: INSTITUTO TECNOLOGICO Y DE ESTUDIOS SUPERIORES DE MONTERREY, Nuevo León (MX); OHIO STATE INNOVATION FOUNDATION, Columbus, OH (US)

(72) Inventors: Raquel Tejeda-Alejandre, Poza Rica (MX); Hernan Lara-Padilla, Sangolqui (EC); Ciro A. Rodriguez, Nuevo León (MX); David Dean, Upper Arlington, OH (US)

(73) Assignees: INSTITUTO TECNOLOGICO Y DE ESTUDIOS SUPERIORES DE MONTERREY, Nuevo Leon (MX); OHIO STATE INNOVATION FOUNDATION, Columbus, OH (US)

( * ) Notice: Subject to any disclaimer, the term of this patent is extended or adjusted under 35 U.S.C. 154(b) by 971 days.

(21) Appl. No.: 16/494,186

(22) PCT Filed: Mar. 15, 2018

(86) PCT No.: PCT/US2018/022746
§ 371 (c)(1),
(2) Date: Sep. 13, 2019

(87) PCT Pub. No.: WO2018/170328
PCT Pub. Date: Sep. 20, 2018

(65) Prior Publication Data
US 2020/0087818 A1   Mar. 19, 2020

Related U.S. Application Data

(60) Provisional application No. 62/471,568, filed on Mar. 15, 2017.

(51) Int. Cl.
*D01D 5/00* (2006.01)
*A61F 2/06* (2013.01)
(Continued)

(52) U.S. Cl.
CPC ............. *D01D 5/0084* (2013.01); *A61F 2/06* (2013.01); *B29C 64/118* (2017.08);
(Continued)

(58) Field of Classification Search
CPC .... D01D 5/0007; D01D 5/0023; D01D 5/003; D01D 5/0038; D01D 5/0046;
(Continued)

(56) References Cited

U.S. PATENT DOCUMENTS

2007/0131235 A1*  6/2007  Janikowski ........ B01D 39/2017
                                                                    131/332
2014/0081414 A1   3/2014  Hall et al.
(Continued)

FOREIGN PATENT DOCUMENTS

WO    2009/101472 A2    8/2009

OTHER PUBLICATIONS

International Search Report and Written Opinion issued by the International Searching Authority (ISA/US) in PCT Application No. PCT/US2018/022746 on Jun. 14, 2018. 9 pages.
(Continued)

*Primary Examiner* — Philip C Tucker
*Assistant Examiner* — Andrew L Swanson
(74) *Attorney, Agent, or Firm* — Meunier Carlin & Curfman LLC

(57) ABSTRACT

Disclosed herein is an apparatus for fabricating a branching structure, the apparatus comprising: a flexible, electrically conductive internal electrical field collector comprising a first collector end, a second collector end, a collector outer surface located between both collector ends, a collector
(Continued)

longitudinal axis extending through the first collector end and the second collector end, and at least one articulating feature positioned between the first collector end and the second collector end, a compression and rotation mechanism in contact with the first collector end, and a continuously formed mandrel that can include branches, having a first mandrel circumference with a mandrel inner circumference larger than the collector outer circumference and positionable over the internal electrical field collector and a second mandrel located at sufficient distance outside the first mandrel to facilitate attraction of electruspun fibers. Also disclosed are methods of manufacturing the branching structure, and grafts thereof.

14 Claims, 20 Drawing Sheets

(51) Int. Cl.
    *B29C 64/118*     (2017.01)
    *B29C 64/188*     (2017.01)
    *B33Y 80/00*     (2015.01)
    *D04H 1/728*     (2012.01)
    *B33Y 10/00*     (2015.01)

(52) U.S. Cl.
    CPC ............ *B29C 64/188* (2017.08); *B33Y 80/00* (2014.12); *D04H 1/728* (2013.01); *A61F 2240/001* (2013.01); *B33Y 10/00* (2014.12); *D10B 2509/06* (2013.01)

(58) Field of Classification Search
    CPC .. D01D 5/0053; D01D 5/0061; D01D 5/0069; D01D 5/0076; D01D 5/0048; D01D 5/0092
    USPC .................................. 269/55–57, 289 R, 294
    See application file for complete search history.

(56) References Cited

U.S. PATENT DOCUMENTS

| | | | |
|---|---|---|---|
| 2014/0141152 A1* | 5/2014 | Sostek | D04H 1/43835 427/2.24 |
| 2016/0047064 A1 | 2/2016 | Khandaker et al. | |
| 2016/0331528 A1* | 11/2016 | Parker | A61F 2/2412 |
| 2018/0245243 A1* | 8/2018 | Krieger | B29C 64/112 |
| 2019/0338445 A1* | 11/2019 | Haff | D01D 5/0092 |

OTHER PUBLICATIONS

Hasan A, Memic A, Annabi N, Hossain M, Paul A, Dokmeci MR, Dehghani F, Khademhosseini A (2014) Electrospun scaffolds for tissue engineering of vascular grafts. Acta Biomater 10:11-25.

Ingavle GC, Leach JK (2014) Advancements in electrospinning of polymeric nanofibrous scaffolds for tissue engineering. Tissue Eng Part B Rev 20:277-93.

Rocco KA, Maxfield MW, Best CA, Dean EW, Breuer CK (2014) In Vivo Applications of Electrospun Tissue-Engineered Vascular Grafts: A Review. Tissue Eng Part B Rev 20:628-640.

Zhang D, & Chang J (2008) Electrospinning of three-dimensional nanofibrous tubes with controllable architectures. Nano letters 8:3283-3287.

Nottelet B, Pektok E, Mandracchia D, Tille JC, Walpoth B, Gurny R, & Moeller M (2009). Factorial design optimization and in vivo feasibility of poly (ϵ-caprolactone)-micro-and nanofiber-based small diameter vascular grafts. J Biomedical Materials Research Part A 89:865-875.

De Valence S, Tille JC, Mugnai D, Mrowczynski W, Gurny R, Möller M, & Walpoth BH (2012) Long term performance of polycaprolactone vascular grafts in a rat abdominal aorta replacement model. Biomaterials 33:38-47.

International Preliminary Report on Patentability issued for Application No. PCT/US2018/022746, dated Sep. 26, 2019.

\* cited by examiner a. Thickness = 254.84μm b. Thickness = 308.94μm
Orientation of Electrospun Fibers THREE DIMENSIONAL PRINTING MODALITY COMBINING FUSED DEPOSITION MODELING AND ELECTROSPINNING

CROSS-REFERENCE TO RELATED APPLICATIONS

This application is a national stage application filed under 35 U.S.C. § 371 of PCT/US2018/022746 filed Mar. 15, 2018, which claims priority to and benefit of U.S. Provisional Application No. 62/471,568, filed Mar. 15, 2017, which is hereby incorporated herein by reference in its entirety.

FIELD

The disclosure generally relates to electrospinning of polymer fibers.

BACKGROUND

There is a wide range of medical treatments that require vascular grafts, for example surgical bypass for atherosclerosis of the major vessels, dialysis access in patients with end-stage renal disease, and pediatric congenital heart defects. Autologous tissue is the graft of choice in most surgical bypass procedures. When autologous tissue is not available in the patient, the next best option is the use of synthetic vascular grafts. See Hasan A, et al., (2014) Acta. Biomater., 10:11-25.

For the particular case of bifurcated vessels, surgeons can use commercial bifurcated synthetic vascular grafts, such as a) the GORE-TEX® Stretch Vascular Graft—Bifurcated (W. L. Gore & Associates, Newark, Delaware, USA), made out of stretched PTFE (commonly known as Teflon™), or b) the Vascutek® Gelsoft™ Bifurcate Grafts (Vascutek Ltd., Renfrewshire, Scotland, UK), based on polyester. However, these options are based on non-resorbable polymers and tubes of uniform dimensions. More limiting is when two tubular grafts have to be connected. Suturing at the roughly right angle connection is difficult and leaves the graft prone to failure at the suture site which is under high flow pressure. Current synthetic vascular grafts therefore present limitations, especially for cases involving vessels with bifurcations and small diameters. See Hasan A, et al., *Acta. Biomater.*, 10:11-25 (2014).

The ideal bifurcated vascular graft would be tissue-engineered to better suit the patient. One limitation in achieving this goal is the limited availability of bifurcated tubular scaffolds based on resorbable materials.

While significant advances have been reported in the use of electrospinning for vascular grafts, both at in vitro and in vivo level, most of the work is limited to tubular shapes. See Hasan A, et al., *Acta. Biomater.*, 10:11-25 (2014); Ingavle G C, et al., *Tissue Eng. Part B Rev.*, 20:277-93 (2014); Rocco K A, et al., *Tissue Eng. Part B Rev.*, 20:628-640 (2014). Zhang and Chang developed a method to build interconnected tubular structures with electrospun mats. Their method is based on guides for the electric field and removable scaffold mandrels. Zhang D, et al, *Nano letters*, 8:3283-3287 (2008).

The compositions and methods disclosed herein address these and other needs.

SUMMARY

Disclosed herein is an apparatus for fabricating a branching structure, the apparatus comprising: a flexible, electrically conductive internal electrical field collector comprising a first collector end, a second collector end, a collector outer surface located between both collector ends, a collector longitudinal axis extending through the first collector end and the second collector end, and at least one articulating feature positioned between the first collector end and the second collector end, a compression and rotation mechanism in contact with the first collector end, and a continuously formed mandrel that can include branches, having a first mandrel circumference with a mandrel inner circumference larger than the collector outer circumference and positionable over the internal electrical field collector and a second mandrel located at sufficient distance outside the first mandrel to facilitate attraction of electruspun fibers.

Also disclosed is a method of making a branching graft, the method comprising:

providing a continuous, branched mandrel, wherein the branching mandrel comprises a first mandrel tubular shape that defines a first mandrel lumen extending along a first mandrel axis, and a second mandrel tube that defines a second mandrel lumen extending along a second mandrel axis, wherein the first mandrel axis creates an angle with the second mandrel axis, positioning the unbranched or branching mandrel on an elongated internal electrical field collector such that the internal electrical field collector extends through the primary (i.e., largest or longest object, i.e., the object with the primary axis for spinning) mandrel lumen, bending the internal electrical field collector away from a longitudinal axis extending through the first end of the electrical field collector and the second end of the electrical field collector, thereby rotating the unbranched or branched mandrel about the first mandrel axis and the second mandrel axis, coating the unbranched or branched mandrel in densely tangled fibers while rotating the internal electrical field collector about the longitudinal axis, thereby forming a branching graft around the branched mandrel, and removing the branched mandrel and the branched graft from the internal electrical field collector.

Further disclosed is a branching graft comprising: a graft wall formed of a single piece of continuous, resorbable material, the graft wall having a first graft tube that extends along a first graft axis and a second graft tube that extends along a second graft axis, wherein the first graft axis creates an angle with the second graft axis. Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 6A shows the computer-aided design (CAD) of the position device. FIG. 6B shows the positioning device with compliant links holding the mandrel and slip ring. FIG. 6C shows the positioning of the mechanism inside an electrospinning chamber.

FIG. 7A shows a scaffold mandrel CAD model. FIG. 7B shows the size and arrangement of an actual mandrel as printed by Fused Modeling Deposition (FDM).

FIG. 10 shows results of an indentation test for an electrosupun membrane generated with internal collector on.

FIG. 16A is a graph showing membrane thickness and strength. FIG. 16B shows tensile strength.

DETAILED DESCRIPTION

Figure 1:
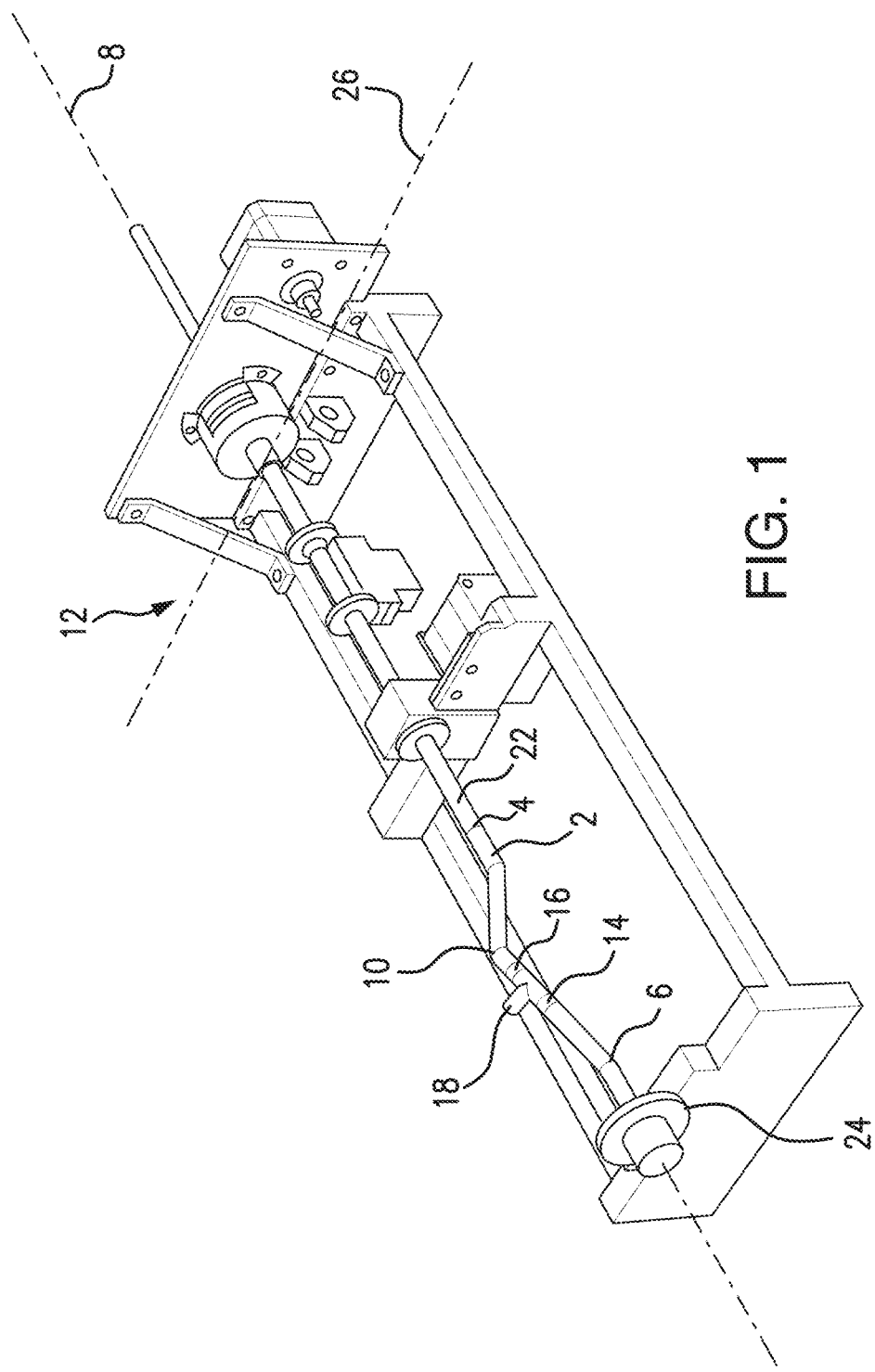
FIG. 1 is a schematic of a positioning device.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular fiber is disclosed and discussed and a number of modifications that can be made to the fiber are discussed, specifically contemplated is each and every combination and permutation of the fiber and the modifications that are possible unless specifically indicated to the contrary. Thus, if a class of fibers A, B, and C are disclosed as well as a class of fibers D, E, and F and an example of a combination fiber, or, for example, a combination fiber comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a composition "may include an second fiber" is meant to include cases in which the formulation includes a second fiber as well as cases in which the formulation does not include a second fiber.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Devices, Methods, and Compositions

Disclosed herein is an apparatus for fabricating a branching structure, the apparatus comprising: a flexible, electrically conductive internal electrical field collector comprising a first collector end, a second collector end, a collector outer surface located between both collector ends, a collector longitudinal axis extending through the first collector end and the second collector end, and at least one articulating feature positioned between the first collector end and the second collector end, a compression and rotation mechanism in contact with the first collector end, and a continuously formed mandrel that can include branches, having a first mandrel circumference with a mandrel inner circumference larger than the collector outer circumference and positionable over the internal electrical field collector and a second mandrel located at sufficient distance outside the first mandrel to facilitate attraction of electruspun fibers.

Importantly, disclosed herein is the 3D printing of the outer surface of the mandrel or single object. The inner mandrel surface can also be 3D printed, but this is not a requirement. For example, one can put material inside the outer surface by any means. The outer surface can also be prepared by non-3D printing means. The 3D printed material can include conductive materials, which if used altogether, can improve the fabrication process. For example, the method can further comprise 3D printing the bifurcated mandrel prior to positioning the unbranched or branching mandrel on an elongated internal electrical field collector. Also disclosed is a method of removing the bifurcated mandrel from the formed unbranched or branching vascular graft.

In one embodiment, the first mandrel axis and the second mandrel axis meet at a reference point, and wherein the method further comprises aligning the origin of an electrospinning nozzle to the reference point.

The branching structure can be, for example, a bifurcated tubular structure. Bifurcation is one of three solutions disclosed herein. The other two are for anisotropic changes in wall shape (i.e., more complex than just change in diameter) and for changes in central axis direction. Taken together, these can allow for the electrospinning of a curving and possibly bifurcating tube that has a non-circular circumference. This can be applied to almost any shape as long as it can be spun about an axis. Examples include oblong, oval, angular, etc. The branches can include such structures as a bifurcation, trifurcation, etc. One of skill in the art will appreciate the various shapes that can be included.

The apparatus can continuously form single objects or a branching mandrels. The objects can solid, such as a solid circumference, or can have an open lattice structure. The compression and rotation mechanism can comprise a rod that extends along the collector longitudinal axis and contacts the first collector end. The compression and rotation mechanism can further comprise a stop that contacts the second collector end. The compression and rotation mechanism can also be capable of translational movement along a transverse axis of the internal electrical field collector.

Also disclosed herein is a method of making a branching graft, the method comprising: providing a continuous, branched mandrel, wherein the branching mandrel comprises a first mandrel tubular shape that defines a first mandrel lumen extending along a first mandrel axis, and a second mandrel tube that defines a second mandrel lumen extending along a second mandrel axis, wherein the first mandrel axis creates an angle with the second mandrel axis, positioning the unbranched or branching mandrel on an elongated internal electrical field collector such that the internal electrical field collector extends through the primary mandrel lumen, bending the internal electrical field collector away from a longitudinal axis extending through the first end of the electrical field collector and the second end of the electrical field collector, thereby rotating the unbranched or branched mandrel about the first mandrel axis and the second mandrel axis, coating the unbranched or branched mandrel in densely tangled fibers while rotating the internal electrical field collector about the longitudinal axis, thereby forming a bifurcated graft around the branched mandrel, and removing the branched mandrel and the branched vascular graft from the internal electrical field collector.

As the internal electrical field collector extends through the primary mandrel lumen, (i.e., largest or longest object, i.e., the object with the primary axis for spinning) the angle increases, and as the size of the branch increases, the control over the weave will decrease. However, the mandel can be rotated in various manners to accommodate for this.

Bending the internal electrical field collector can comprise activating at least one articulating feature on the internal electrical field collector. Bending the internal electrical field collector can also comprise compressing or stretching the internal electrical field collector along the main or a branch's longitudinal axis.

The length of the internal electrical field collector can change along the longitudinal or a branch's axis. Bending the internal electrical field collector can comprise translating the internal electrical field collector along a transverse axis extending perpendicular to the longitudinal axis.

In one embodiment, the length of the internal electrical field collector changes along the transverse axis. Bending the internal electrical field collector can comprise compressing or stretching the internal electrical field collector along a longitudinal axis and translating the internal electrical field collector along a transverse axis. Coating the mandrel in densely tangled to fully organized weave of fibers can further comprise depositing the fibers by an electrospinning process.

Disclosed herein is a branching graft comprising: a graft wall formed of a single piece of continuous, resorbable material, the graft wall having a first graft tube that extends along a first graft axis and a second graft tube that extends along a second graft axis, wherein the first graft axis creates an angle with the second graft axis.

In the claims herein, it is noted that the grafts can be for a variety of uses and purposes in the human body. Examples include, but are not limited to, tubular tracts such as the digestive tract, oropharyngeal tract, nasal tract, reproductive tracts, ventricular tracts, valvular structures along tubular tracts, vascular structures within and outside organs, tubular structures in other organs that include nervous, body humor transmitting or filtering, structural, or sensory tissues. Also disclosed are machine tubular structures for engine, heating, cooling, hydraulic, or other mechanical devices.

In one example, the first graft tube meets the second graft tube at an intersection point, and wherein the intersection point is devoid of sutures or adhesives. The first graft axis and second graft axis can be perpendicular, or can be non-perpendicular, and exist at any angle to each other, such as 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, 120, or more degrees with respect to each other.

One of skill in the art will appreciate that any material can be used, such as a continuous, porous mat of densely tangled fibers. The material can be electrospun, for example. The material can be polycaprolactone.

In one embodiment, the first graft tube comprises a first graft outer diameter and the second graft tube comprises a second graft outer diameter, wherein the first graft outer diameter and the second graft outer diameter differ by a factor greater than 10%, such as 20, 30, 40, 50%, or more.

The graft wall of the first graft tube can comprise a first graft thickness, the graft wall of the second graft tube comprises a second graft thickness, and wherein the first graft thickness and the second graft thickness differ by a factor greater than 10%, such as 20, 30, 40, 50%, or more.

With reference to FIG. 1, an apparatus according to one embodiment is used for fabricating a bifurcated structure. The apparatus comprises a flexible, electrically conductive internal electrical field collector 2 comprising a first collector end 4, a second collector end 6, a collector outer diameter, a collector longitudinal axis 8 extending through the first collector end and the second collector end, and at least one articulating feature 10 positioned between the first collector end and the second collector end. The apparatus further comprises a compression and rotation mechanism 12 in contact with the first collector end. The apparatus also comprises a continuously formed bifurcated mandrel 14 having a first mandrel tube 16 with a mandrel inner diameter larger than the collector outer diameter and positionable over the internal electrical field collector and a second mandrel tube 18 extending away from the first mandrel tube at an angle.

The continuously formed bifurcated mandrel 14 can have an open lattice structure 20. The compression and rotation mechanism 12 can comprise a rod 22 that extends along the collector longitudinal axis and contacts the first collector end 4. The compression and rotation mechanism 12 can further comprise a stop 24 that contacts the second collector end 6. The compression and rotation mechanism 12 can also be capable of translational movement along a transverse axis 26 of the internal electrical field collector 2.

Figure 2:
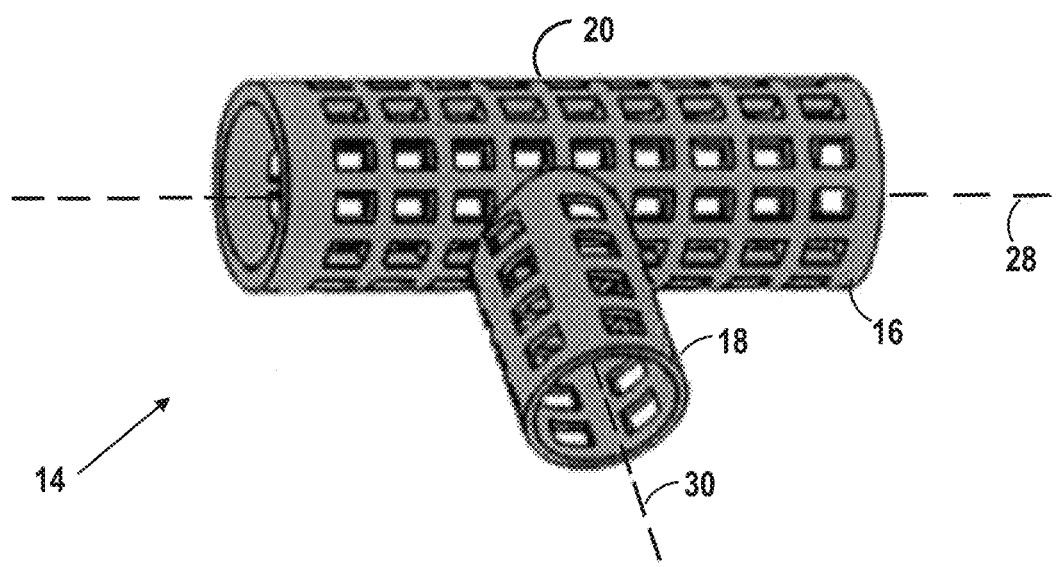
FIG. 2 is a scaffold mandrel CAD model.

With reference to FIG. 2, the continuous, bifurcated mandrel 14 can comprise a first mandrel tube 16 that defines a first mandrel lumen extending along a first mandrel axis 28, and a second mandrel tube 18 that defines a second mandrel lumen extending along a second mandrel axis 30. The first mandrel axis can create an angle with the second mandrel axis.

Figure 3:
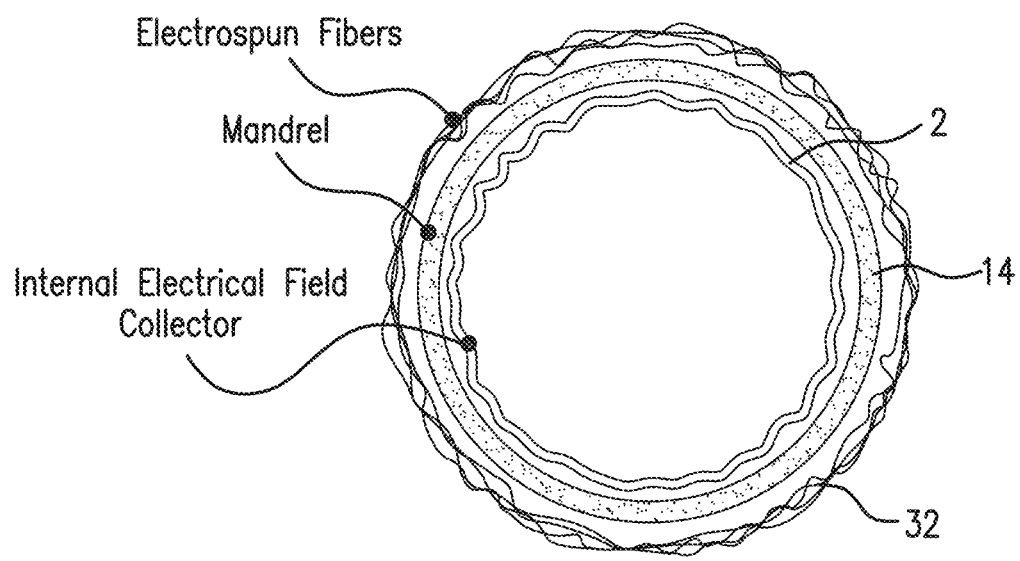
FIG. 3 is a schematic showing a scaffold cross section during the electrospinning process, further showing the arrangement of the internal electrical field collector.

With reference to FIG. 3, the bifurcated mandrel 14 can be coated in densely tangled fibers while rotating the internal electrical field collector 2 about the longitudinal axis, thereby forming a bifurcated vascular graft 32 around the bifurcated mandrel.

Figure 4:
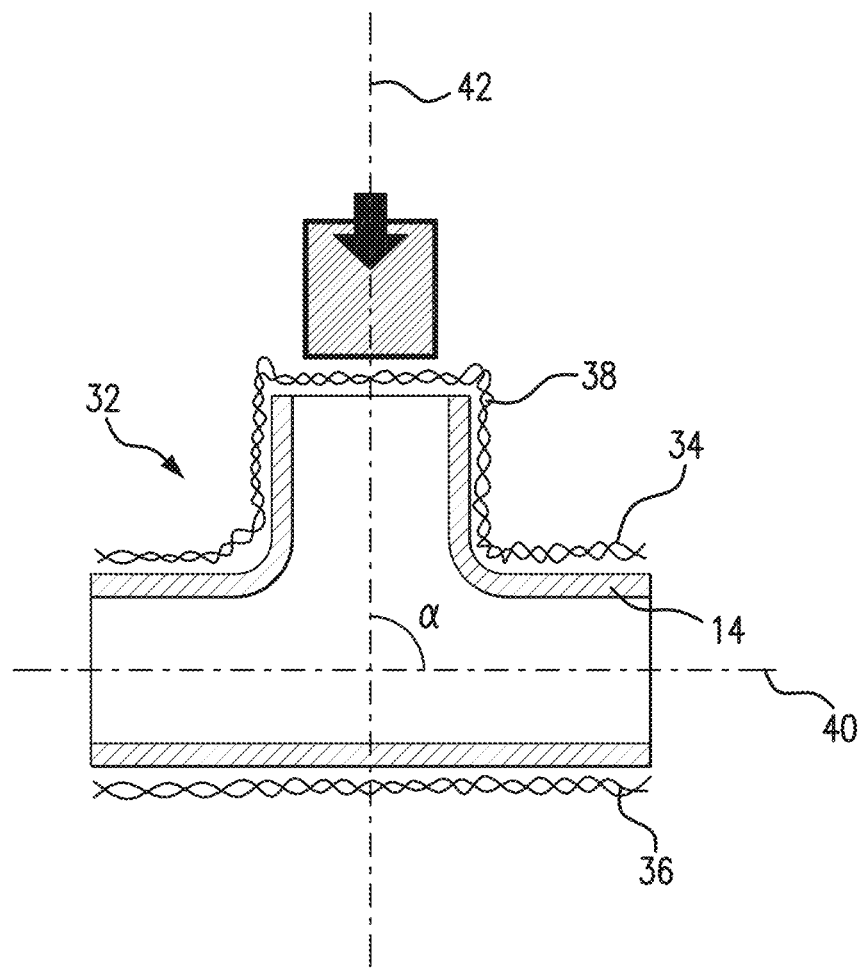
FIG. 4 is a schematic showing a scaffold side view, further showing the angle in a bifurcated structure.

With reference to FIG. 4, the bifurcated vascular graft 32 can comprise a graft wall formed of a single piece of continuous, resorbable material 34, the graft wall having a first graft tube 36 that extends along a first graft axis 40 and a second graft tube 38 that extends along a second graft axis 42, wherein the first graft axis creates an angle α with the second graft axis.

The fabrication device is typically constructed of materials which are not electrically conductive. Such materials avoid undesirable interference with the electrically conductive internal electrical field collector during the graft formation process (e.g., electrospinning process). Any solid, non-electrically conductive materials can be used which can provide the shape and utility of the fabrication device. For example, wood, plastic, composites, adhesives, cements, plasters, and other materials can be used. In some embodiments, the fabrication device is comprised of wood and/or plastic.

The electrically conductive internal electrical field collector can be comprised of one or more electrically conductive materials. For example, the electrically conductive internal electrical field collector can be comprised of metals, alloys, conductive gels, or other such materials. In some embodiments, the electrically conductive internal electrical field collector can be comprised of one or more metals such as silver, copper, gold, copper, or aluminum (e.g., aluminum foil). The electrically conductive internal electrical field collector can be comprised of a continuous material, or can be a collection of one or more materials packed in a regular or irregular arrangement (e.g., packed foil or a mesh of wires). During the process of making a bifurcated vascular graft, a voltage can be applied to the electrically conductive internal electrical field collector.

The fabrication apparatus contains at least one articulating feature positioned between the first collector end and the second collector end.

The fabrication apparatus further comprises a compression and rotation mechanism in contact with the first collector end.

The electrically conductive internal electrical field collector is positioned within at least a portion of the lumen of the continuously formed bifurcated mandrel. Thus, the mandrel contains a first mandrel tube with an inner diameter larger than the collector outer diameter and positionable over the internal electrical field collector. For example, the electrically conductive internal electrical field collector can be positioned on the inner luminal surface of the first mandrel tube. In some or further embodiments, the electrically conductive internal electrical field collector can substantially fill the lumen of the first mandrel tube. The mandrel further comprises a second mandrel tube extending away from the first mandrel tube at an angle. The electrically conductive internal electrical field collector can also be positioned on the inner luminal surface of the second mandrel tube. In some or further embodiments, the electrically conductive internal electrical field collector can substantially fill the lumen of the second mandrel tube.

The continuously formed bifurcated mandrel can have various forms of surface structure. In some embodiments, the bifurcated mandrel can have a continuous, closed structure. In some embodiments, the bifurcated mandrel can have openings within the structure. In some embodiments, the openings within the structure can be irregular, or alternatively, regular or repeating in pattern. In some embodiments, the bifurcated mandrel can have an open lattice structure.

The angle α can be any angle greater than zero degrees. In some embodiments, the angle α is from 1 degree to 90 degrees. In some embodiments, the angle α is from 10 degrees 10 degrees to 80 degrees, or from 30 degrees to 60 degrees. In some embodiments, the angle α is about 90 degrees such that the first graft axis and second graft axis are substantially perpendicular. In some embodiments, the angle α is less than about 90 degrees such that the first graft axis and second graft axis are non-perpendicular.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

This example provides methods for the fabrication of resorbable, bifurcated vascular grafts by combining electrospinning and 3D printed mandrels that are patient-specific shapes, including bifurcations.
Materials and Methods
Conceptual Design.

Figure 5A:
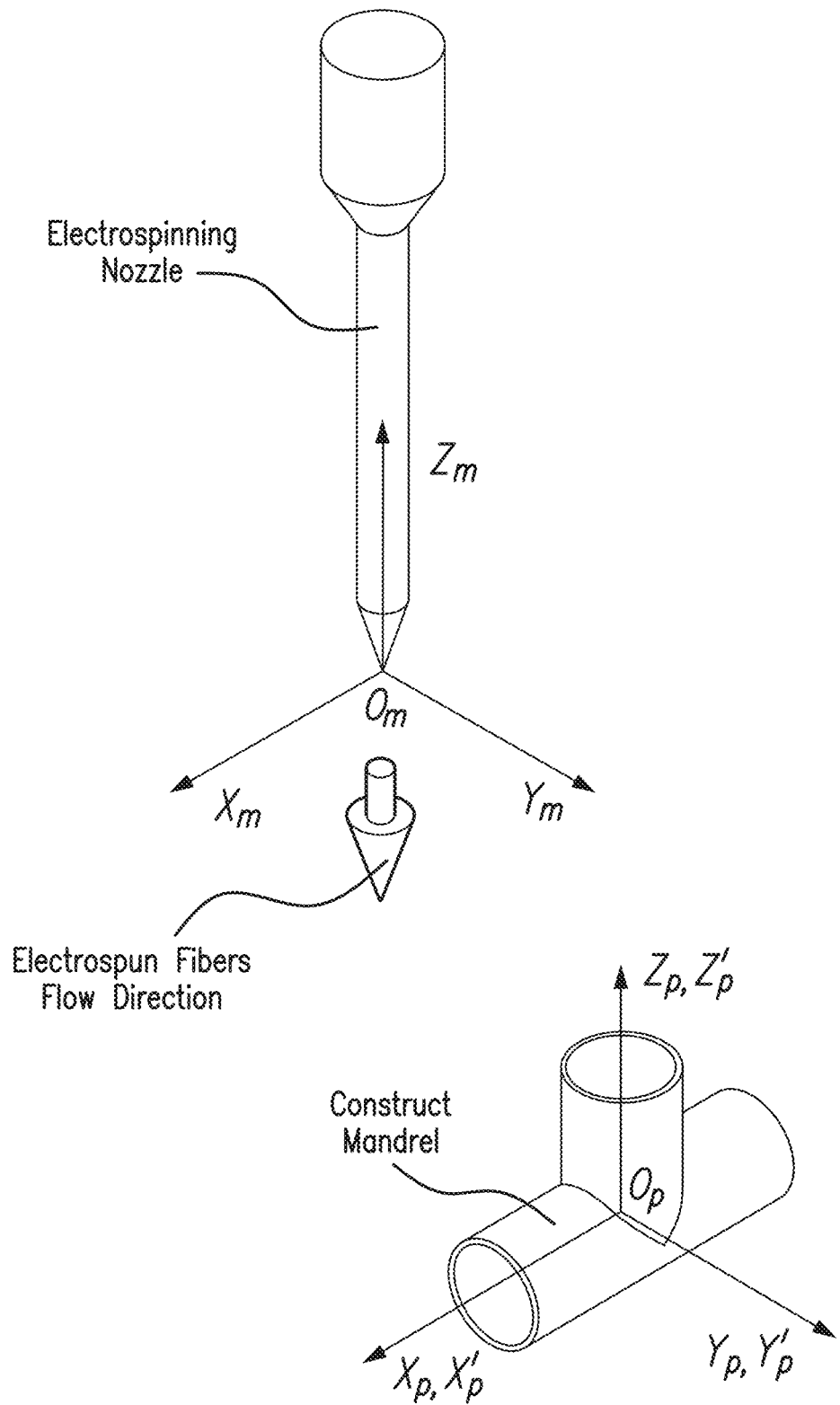
FIGS. 5A and 5B are schematics showing the coordinate system for the electrospinning machine and the mandrel (FIG. 5A), and the nomenclature for mandrel rotations (FIG. 5B).
Figure 5B:
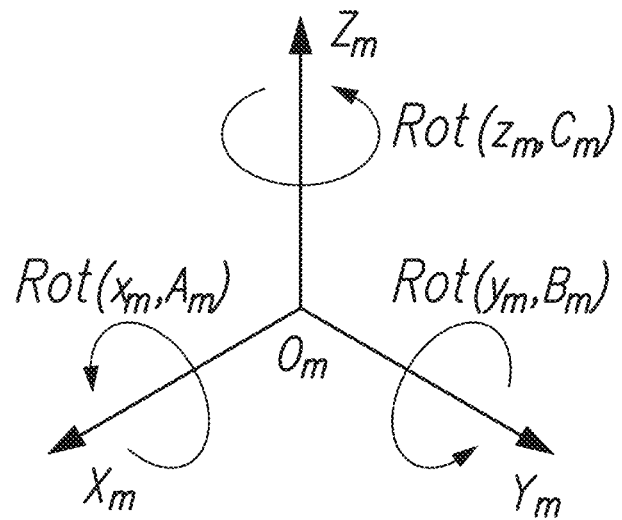
Figure 5B:
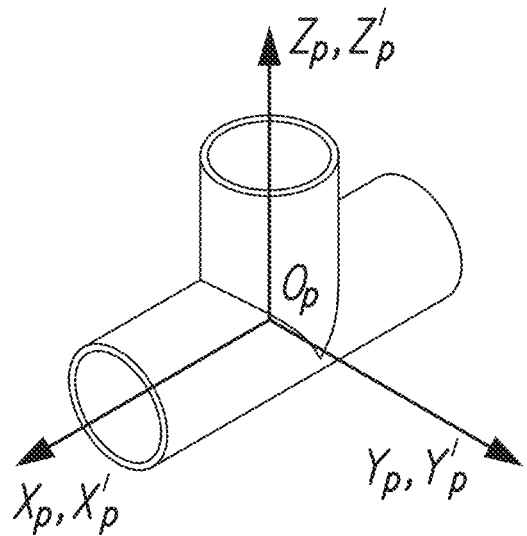
Figure 5B:
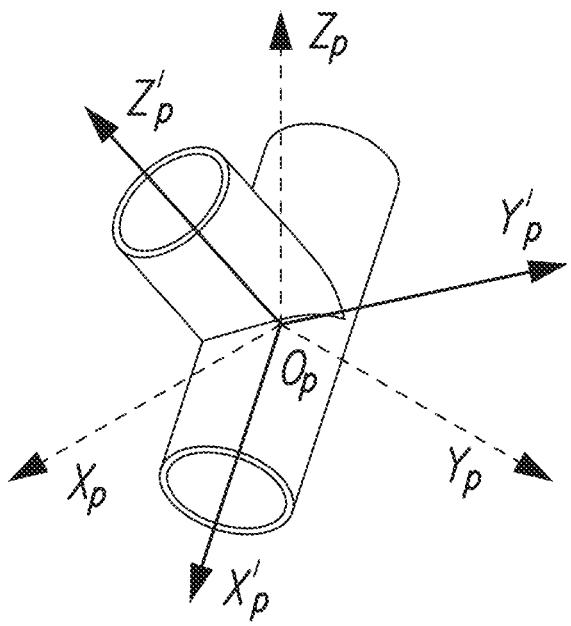

The basic concept is the use of a directed electrical field and dynamic positioning of the construct, as shown in FIG. 3, FIG. 5A, and FIG. 5B. With correct positioning, the electrospun fibers can generate a mat with a weave as complex, or more complex, than traditionally spraying onto a single diameter mandrel. The 3D mandrel included a bifurcated tubular shape, as an internal electrical field collector pulls them. The mandrel could be 3D printed from inert material and removed. It could be made out of resorbable polymer and be part of the final synthetic vascular graft, or it could be an object which is effectively dissolved within the external, 3D printed sheet. Alternatively, the mandrel could be removed, if the graft can stretch, leaving only the electrospun membrane to form the graft. The internal electrical field collector was removed from the construct after electrospinning.

Specific kinematics positioned the mandrel with respect to the direction of the electrospun fibers' flow. FIG. 5A shows the machine coordinate system $(x_m, y_m, z_m,)$, defined with an origin $(O_m)$ at the tip of the electrospinning nozzle. The reference point on the part $(O_p)$ was located at the intersection of the bifurcated axes. The short tubular T shape was concentric with the $z_p$ part axis.

The intended positioning system provided at least two degrees of freedom to rotate the mandrel in the A direction (around the $x_m$ machine axis), and, simultaneously, the device positioned the mandrel in the B direction (around the $y_m$ machine axis), as shown in FIG. 5B. The system allowed for continuous rotation and/or the indexing of specific angular positions. Ideally, the part origin $(O_p)$ could be aligned with the electrospinning nozzle $(x_m=0$ and $y_m=0)$.

The combination of directed electrical field and dynamic positioning of the construct produced a semi-uniform mat of electrospun fibers on top of a bifurcated tubular mandrel.
Positioning Device.

Figure 6A:
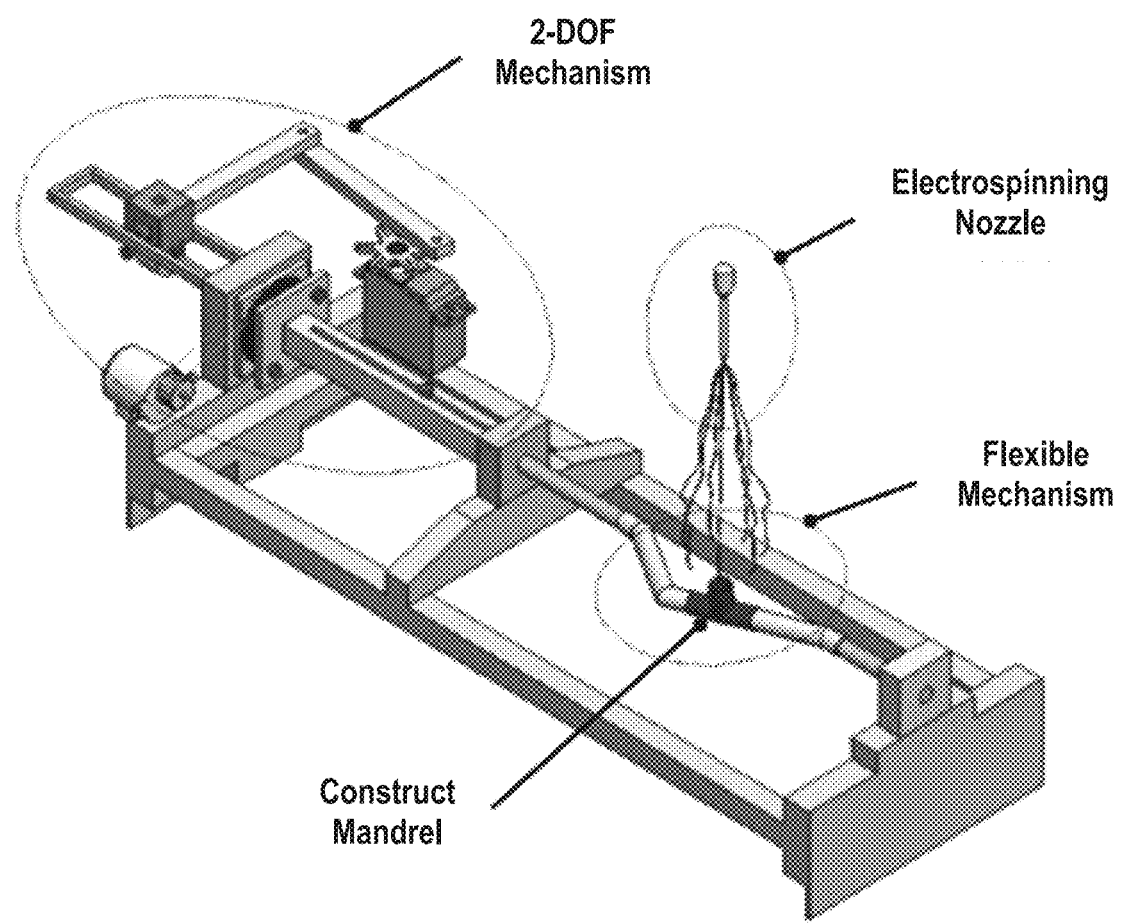
FIG. 6A through 6C are schematics and images showing the components and spatial arrangement of the positioning device.
Figure 6B:
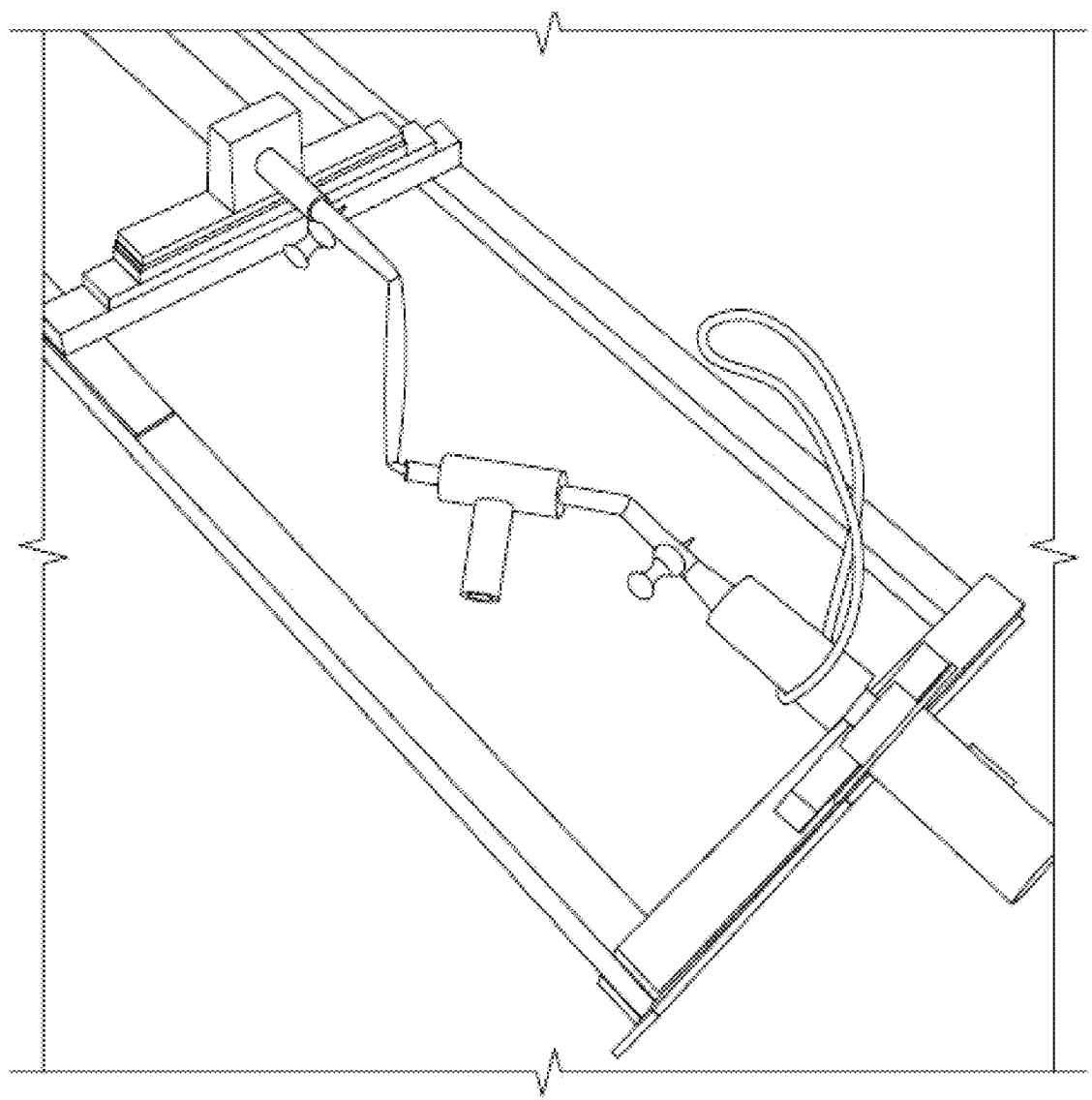

The conceptual design was reduced to practice, including the positioning device shown in FIG. 6A. Balsa wood and plastic were used to avoid interference with the electrospinning electrical field. FIG. 6B shows how the orientation along the B direction was achieved through a simple compliant mechanism with flexible joints. The compliant mechanism was actuated through an axial motion along the main rotating axis A (rod in FIG. 6A). Control was achieved through Arduino.

Figure 6C:
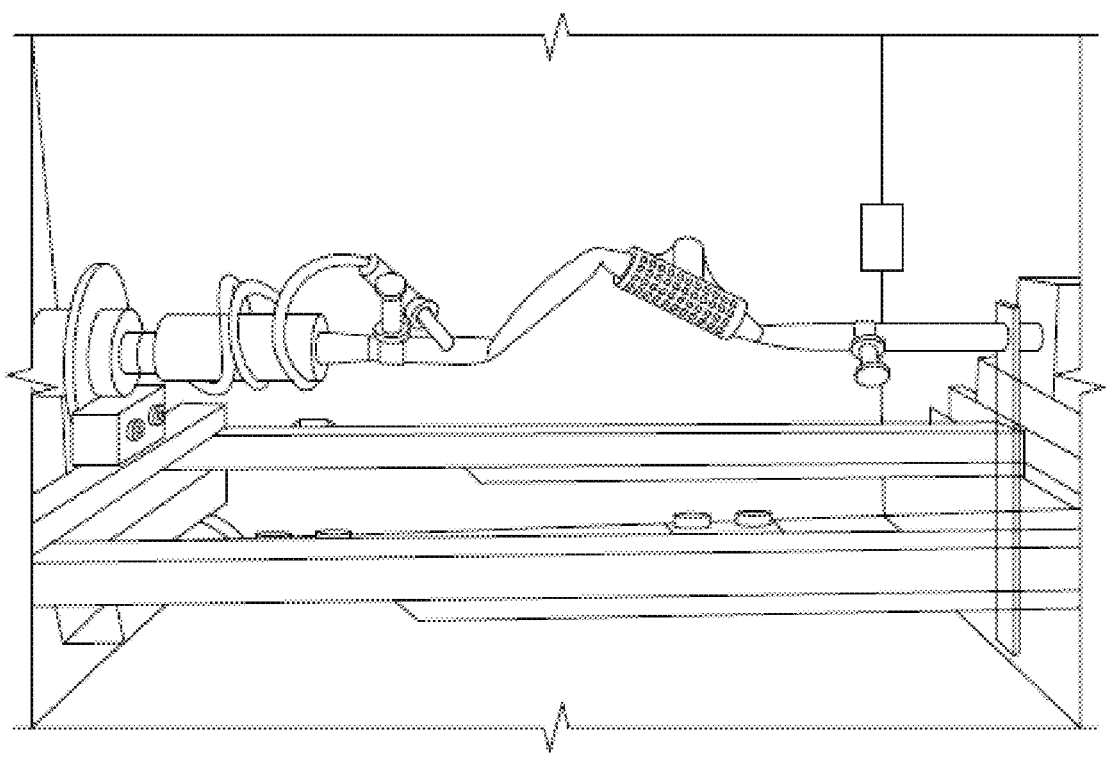
Figure 7A:
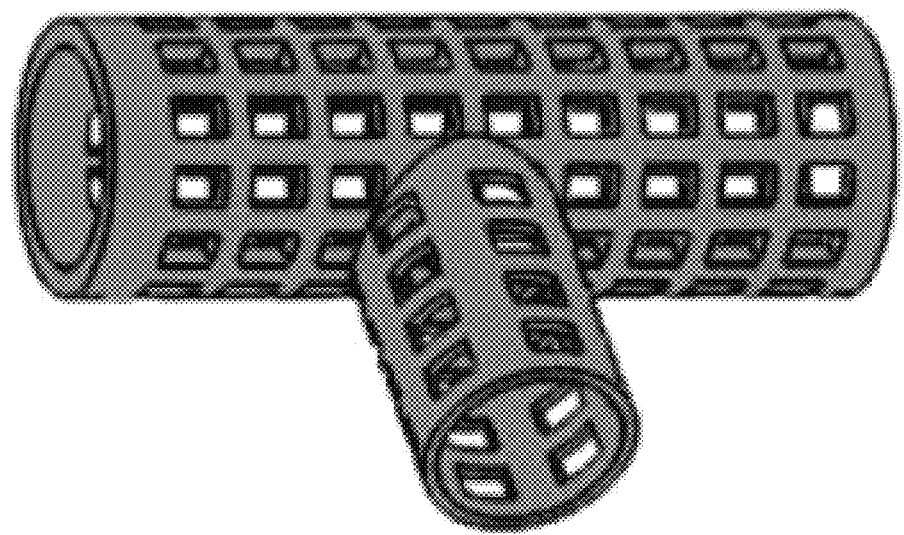
FIGS. 7A and 7B are schematics and images showing example mandrels.
Figure 7B:
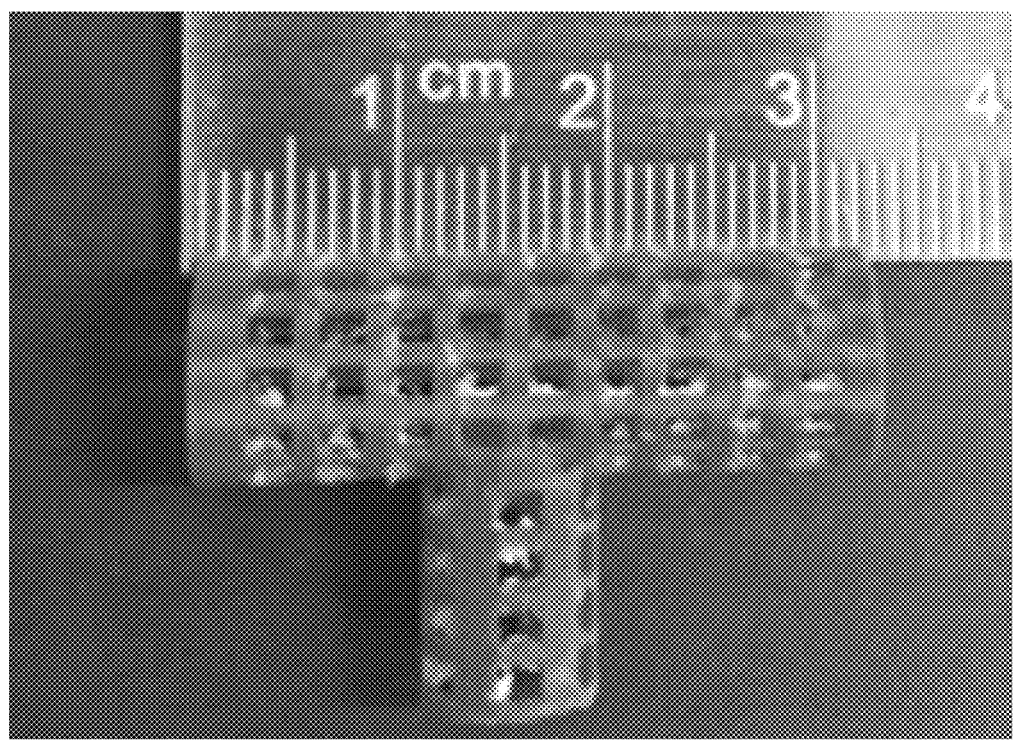
Figure 8:
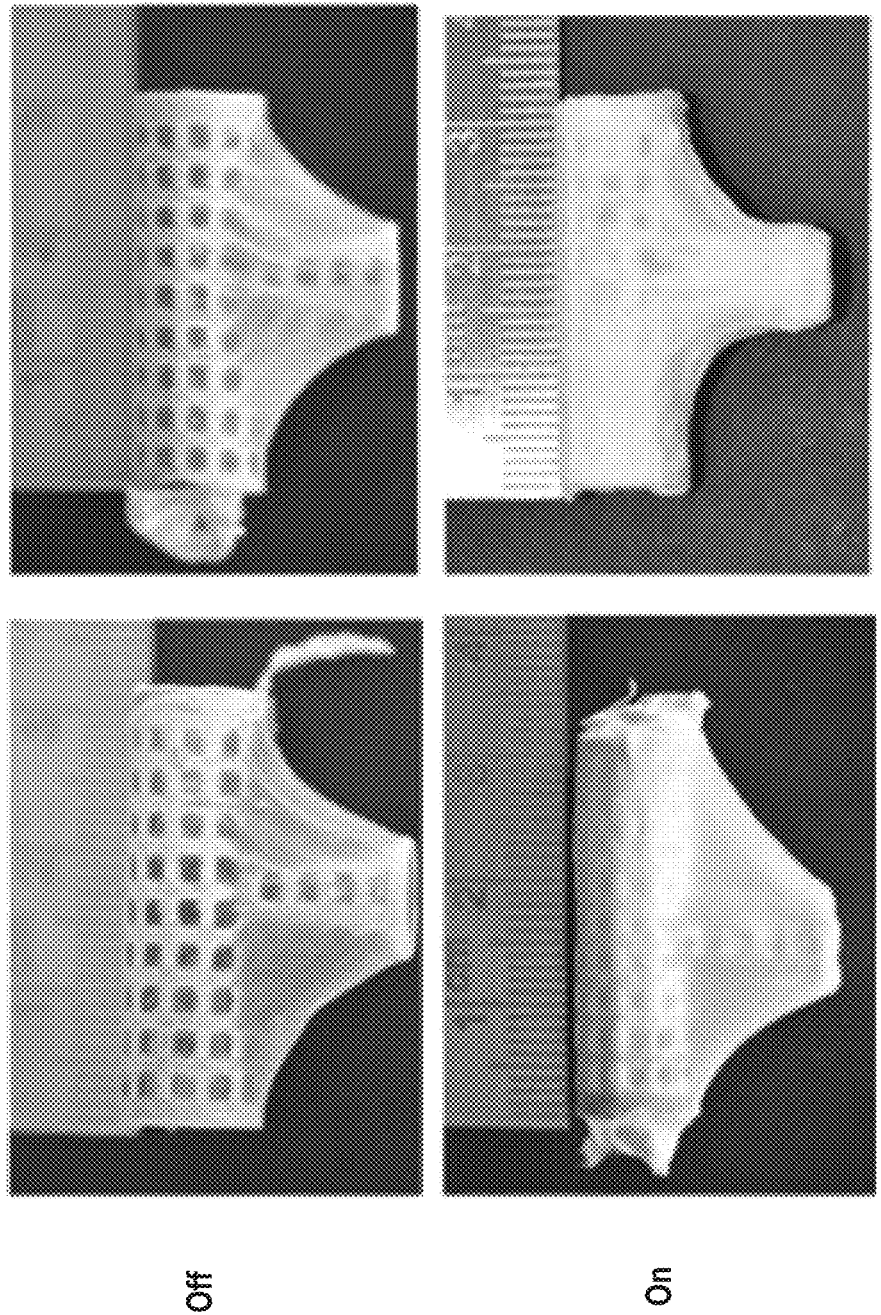
FIG. 8 is a set of images showing bifurcated tubular scaffolds for different experimental conditions. The images show results obtained when the mandrel positioning is fixed at 0° in the B direction (left column) or when indexed at 0° and −60° (right column) when the internal electrical field collector is either off (top row) or on (bottom row).

FIG. 6C shows positioning of the device inside an acrylic enclosure. The motors were isolated from the main electrospinning chamber by an adjustable acrylic wall. The internal electrical field collector was formed with aluminum foil. Voltage was delivered to the internal collector through the slip ring system at the left side of the picture.
Process Parameters
Scaffold Mandrel.

The mandrel was generated through Fused Modeling Deposition (FDM) with a Stratatys Fortus 400 machine and standard acrylonitrile butadiene styrene (ABS) material was used. The mandrel was designed with an open structure to facilitate electrical field flow. Internal diameters of 10.00 and 8.22 mm were used for the main tubular section and the T section, respectively. Wall thickness was about 1 mm.
Electrospinning Process.

The electrospinning solution was based on polycaprolactone (PCL) (at 10% w) and acetone, with stirring at 45° C. for 4 hrs. The solution was delivered with a syringe infusion pump (model KS 100 (KD Scientific Inc., Holliston, MA).

The power source had a maximum voltage of 20 kV and maximum current of 250 µA (model ES20P-5W, Gamma High Voltage Research Inc., Ormond Beach, Florida, USA). The specific electrospinning parameters used are listed in Table 1, including the positioning and rotation kinematics.

For the experimental design, only two variables were considered: whether the internal electric field collector was on or off, and the mandrel positioning in the B direction (Table 1). Five replications were used.

TABLE 1

Electrospinning process parameters.

| Fixed Parameters | |
|---|---|
| Voltage, V [kV] | 18 |
| Electrospinning Nozzle, $D_e$ [mm] | 0.86 |
| Solution Flow Rate, $Q_e$ [ml/h] | 7 |
| Electrospinning Time, $t_e$ [min] | 10 |
| Part Location (Nozzle Height), $z_m$ [mm] | 150 +/− sinusoidal (20 mm amplitude) |
| Part Location, $x_m$ [mm] | 0 |
| Part Location, $y_m$ [mm] | 0 +/− sinusoidal (20 mm amplitude) |
| Part Rotation, $\omega_A$ [rad/s] | 0.45 |
| Variable Parameters | |
| Internal Electric Field Collector | On/Off |
| Mandrel Positioning in B Direction | Fixed at 0°/Indexing at 0° & −60° |

Characterization of Bifurcated Tubular Scaffolds
Qualitative Analysis.

The bifurcated scaffolds were analyzed via optical microscopy and SEM imaging. Overall density of electrospun membranes and scaffold integrity were evaluated for different process conditions.

Mechanical Properties.

Preliminary evaluation of mechanical properties was conducted for the bifurcated scaffolds. As shown in FIG. 6A, the construct location on the positioning device left the T section open to the electrospun fiber deposition. An indentation test was devised to test the maximum load allowed by the membrane of electrospun fibers generated at the end of the T section.

A universal machine Instron 3365 (Norwood, Massachusetts, USA) was used for indentation tests (5 N load cell and hexagonal rod with a flat end) and tension tests (1 kN load cell).

Results

Figure 9A:
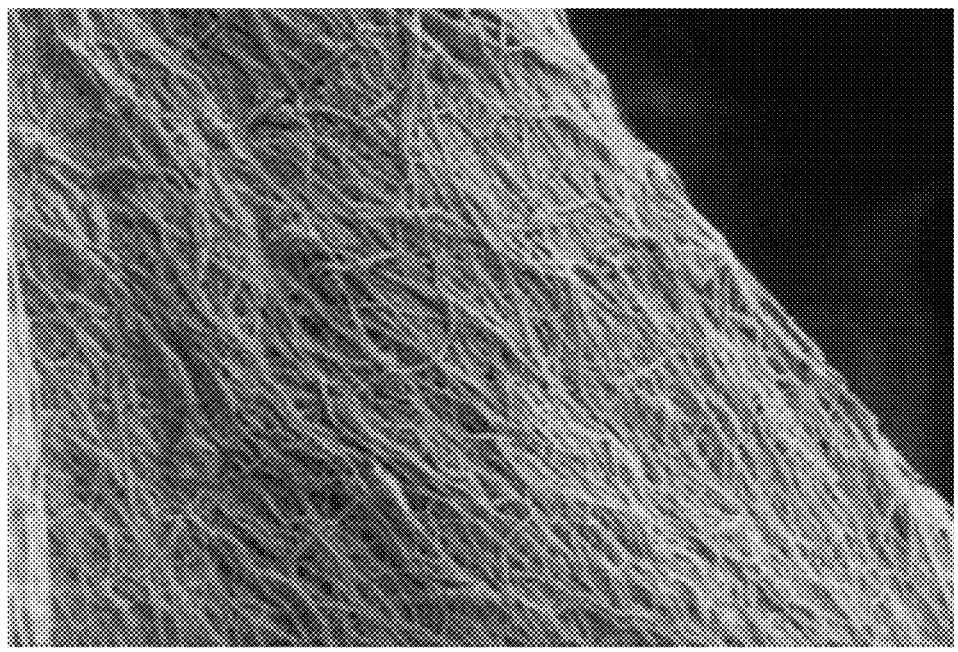
FIG. 9A through 9C are scanning electron micrographs (SEM) of electrospun fibers on a bifurcated tubular scaffold. The micrographs show the weaving of electrospun fibers at varying degrees of zoom, as shown by the scale bars of 20 μM in FIG. 9A and FIG. 9B, and 2 μm in FIG. 9C.
Figure 9B:
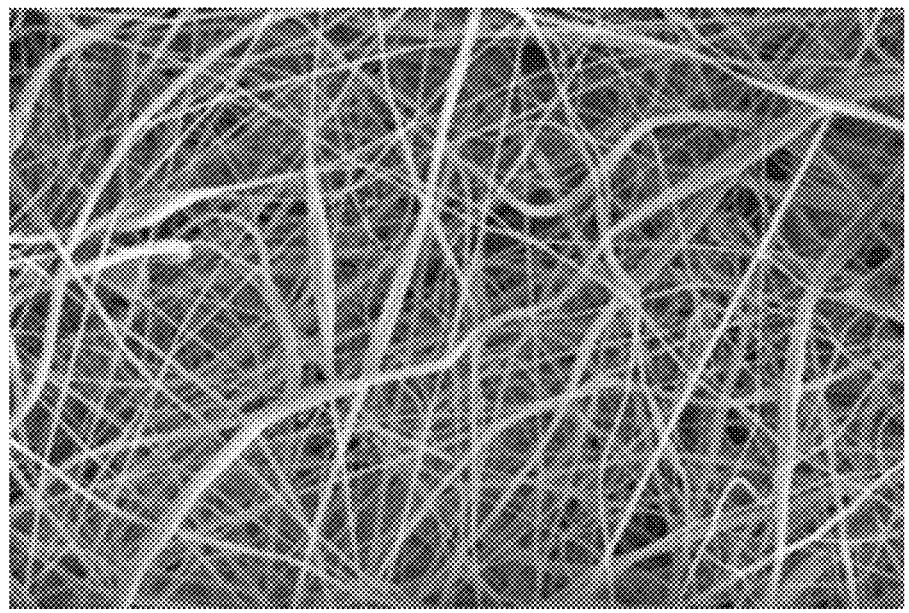
Figure 9C:
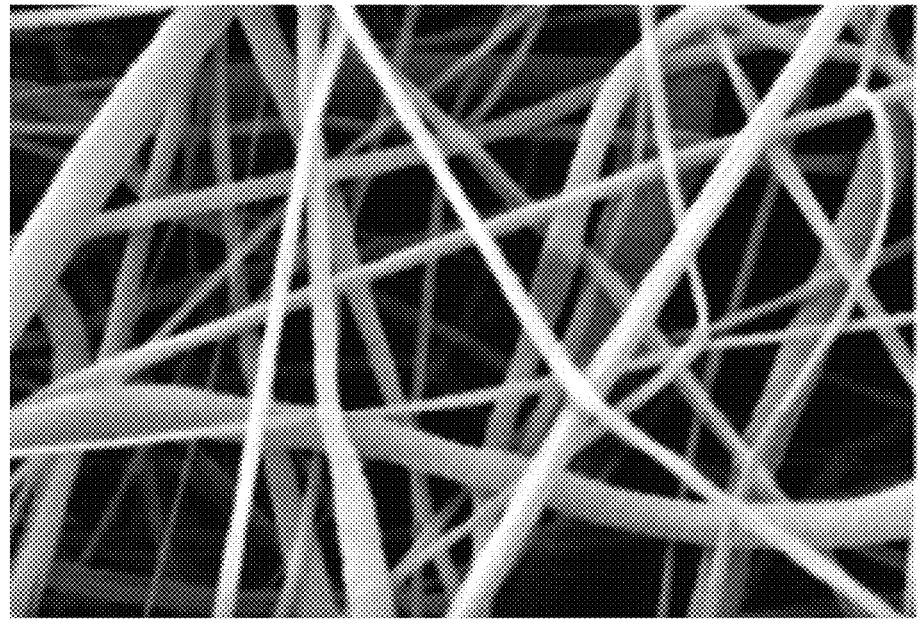

Table 1 shows a representative sample scaffold for each combination of variable parameters. From a qualitative point of view, there is a clear advantage in combining an internal electrical field collector with mandrel kinematics that combine rotation around $x_m$ machine axis (A direction, as defined in FIG. 5) and positioning around $y_m$ machine axis (B direction, as defined in FIG. 5). FIG. 9A through 9C show consistent weaving of dense fiber, interwoven, and electrospun mats.

Figure 10:
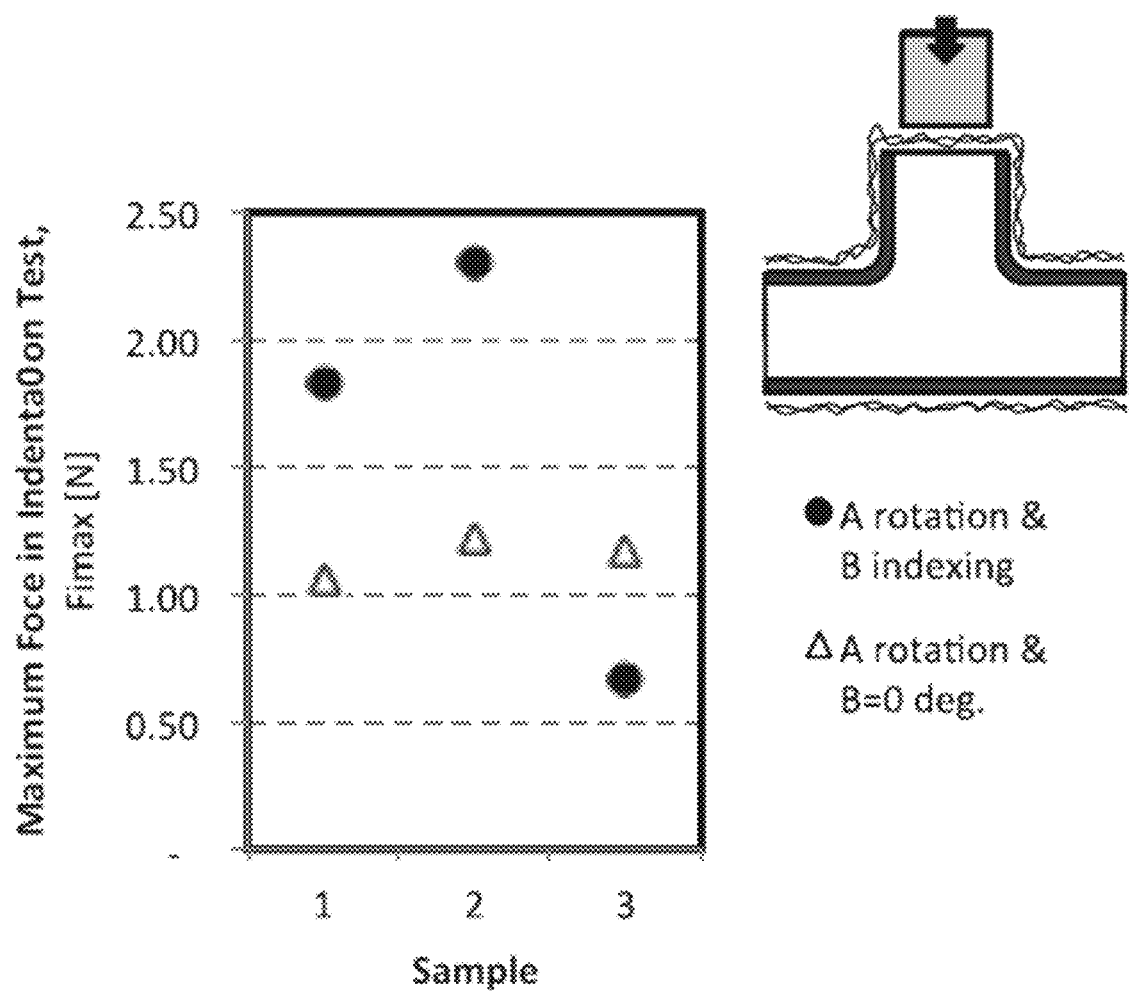

Results for mechanical properties are shown in FIG. 10 (indentation testing). Only those samples with experimental conditions corresponding to the internal collector were tested for mechanical properties. Electrospun membranes generated without the use of an internal collector were too weak for this testing.

Tension tests showed average maximum strengths of 2.74 MPa in samples with internal collector and indexing in B direction vs. 1.21 MPa in samples with internal collector and no indexing in B direction. The average scaffold membrane thickness was 170 mm vs. 150 mm, respectively.

DISCUSSION

Disclosed herein are a robotically controlled electrospinning fiber source and the electrical control of both the mandrel and the electrospun fiber source. The shape of the final scaffold corresponded well to the intended bifurcated tube (see Table 1). These results show that a user can maintain the use of internal electrical field collector and dynamic positioning of the mandrel to generate improved results.

Conventional tubular scaffolds have strengths in the range of 3 and 4 MPa in order to be considered adequate for in vivo testing as vascular grafts inside models. Nottelet B, et al., *J. Biomedical Materials Research Part A*, 89:865-875 (2009); de Valence S, et al., *Biomaterials*, 33:38-47 (2012). The resulting scaffolds disclosed herein showed maximum strengths over 50% of conventional tubular scaffolds with similar electrospinning materials.

Figure 11A:
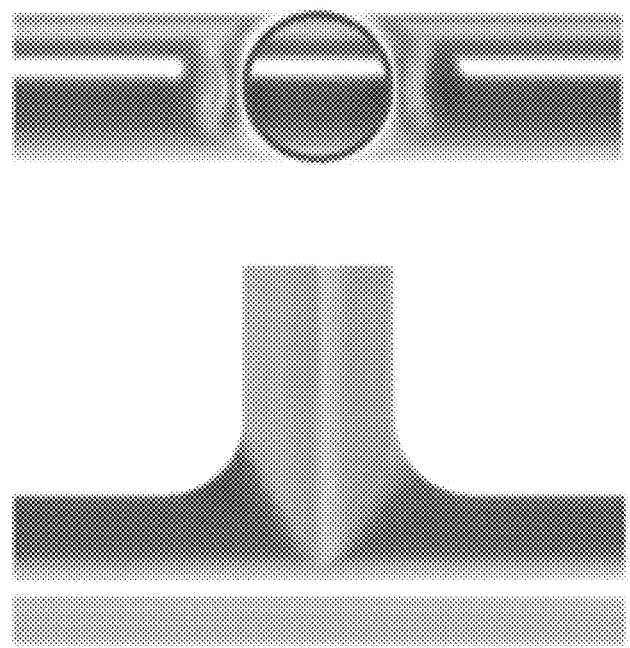
FIGS. 11A and 11B are images showing a scaffold in a T shape (FIG. 11A) and in a Y shape (FIG. 11B).
Figure 11B:
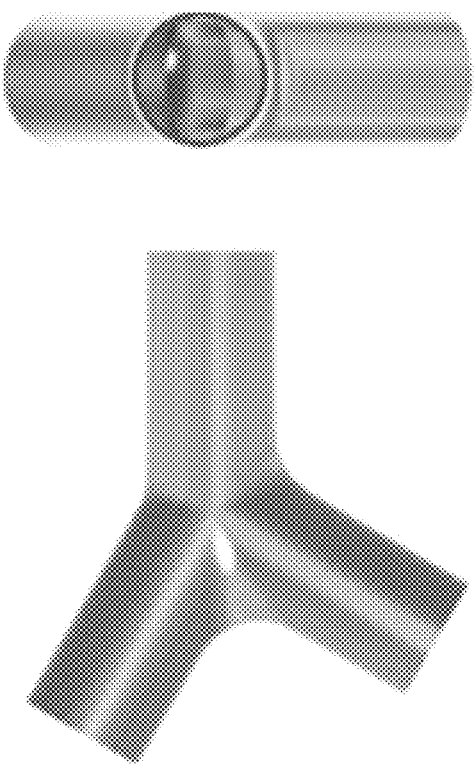
Figure 12:
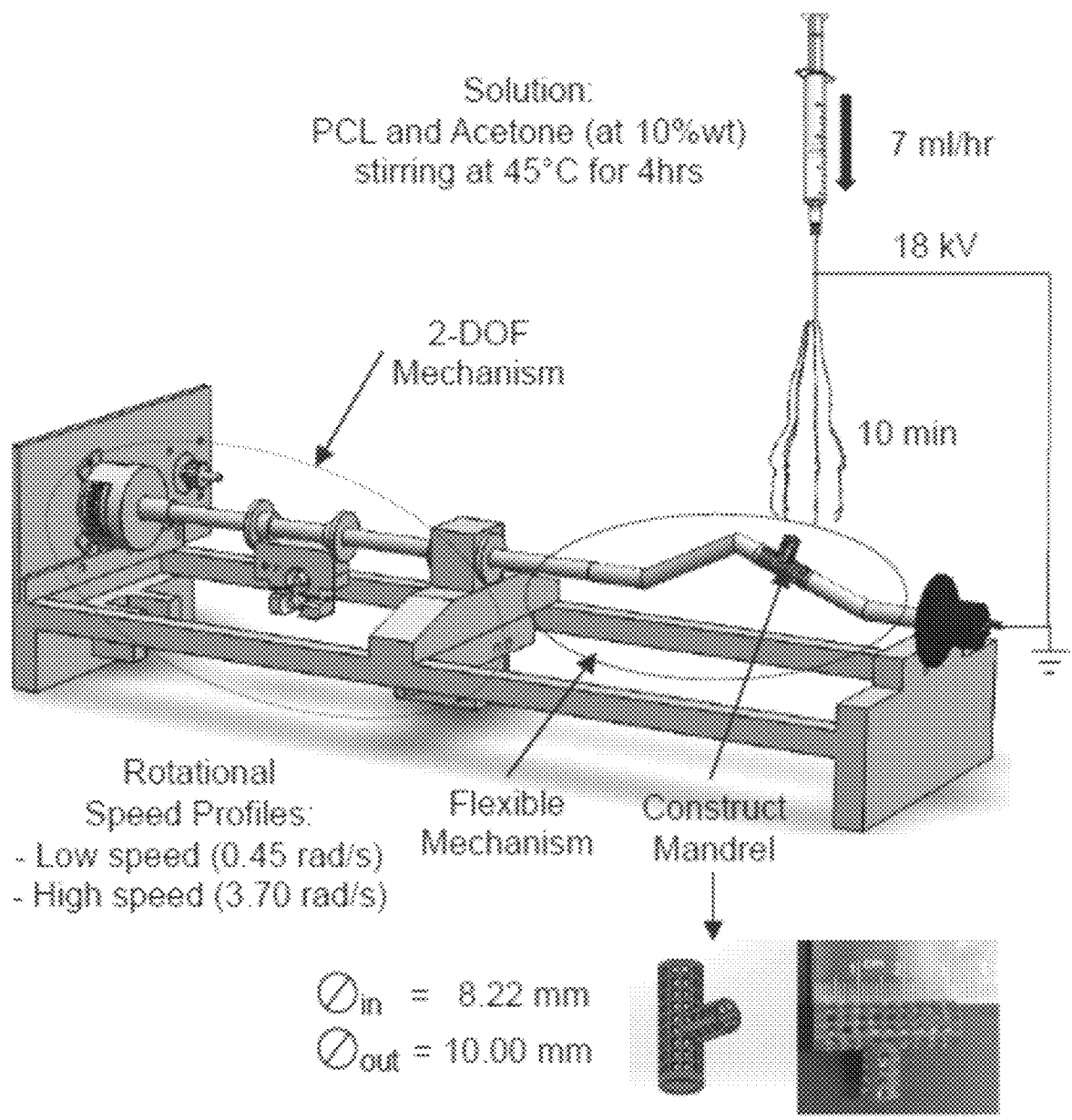
FIG. 12 shows the construction of electrospun bifurcated tubular scaffolds (EBTS) and the experimental conditions used.
Figure 13:
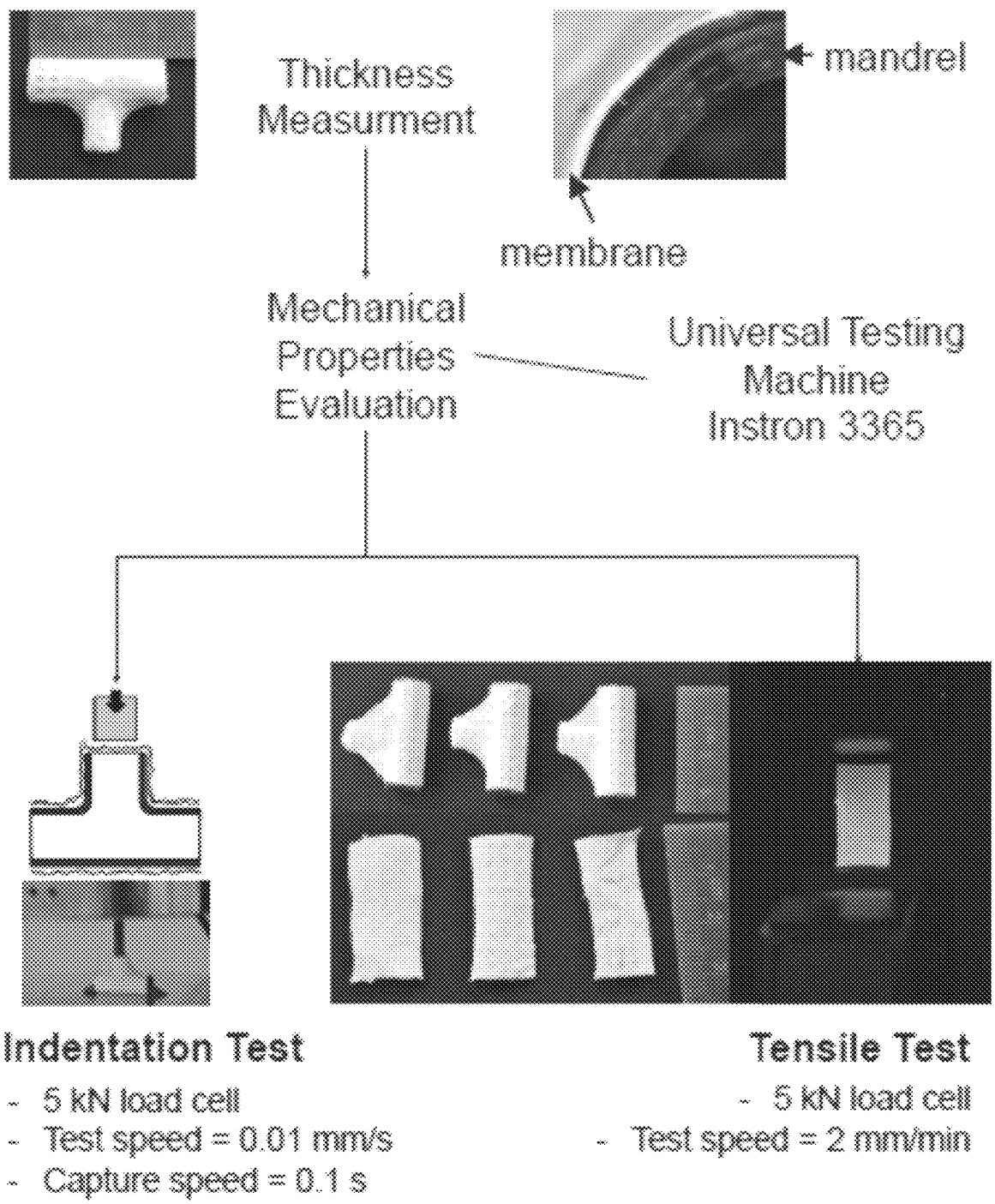
FIG. 13 shows the characterization of EBTS, including physical and mechanical properties.
Figure 14:
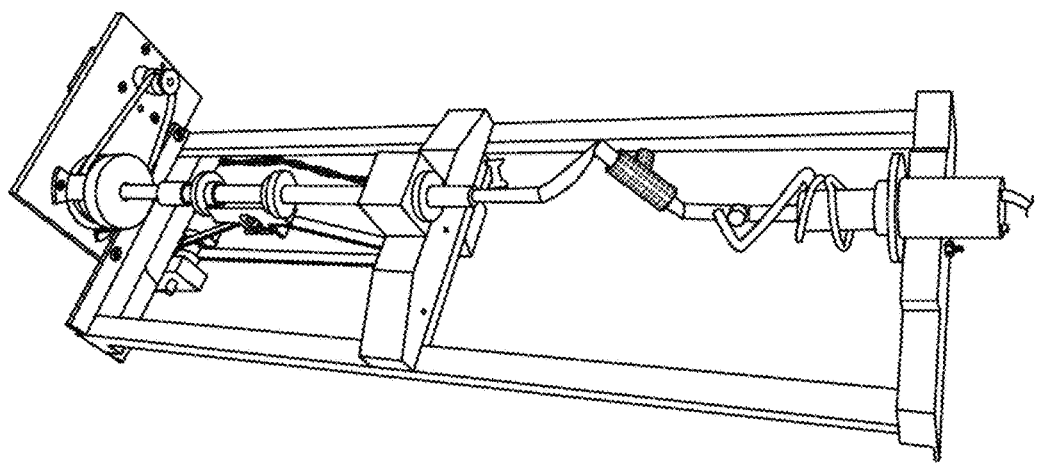
FIG. 14 is an image showing the positioning device.
Figure 15:
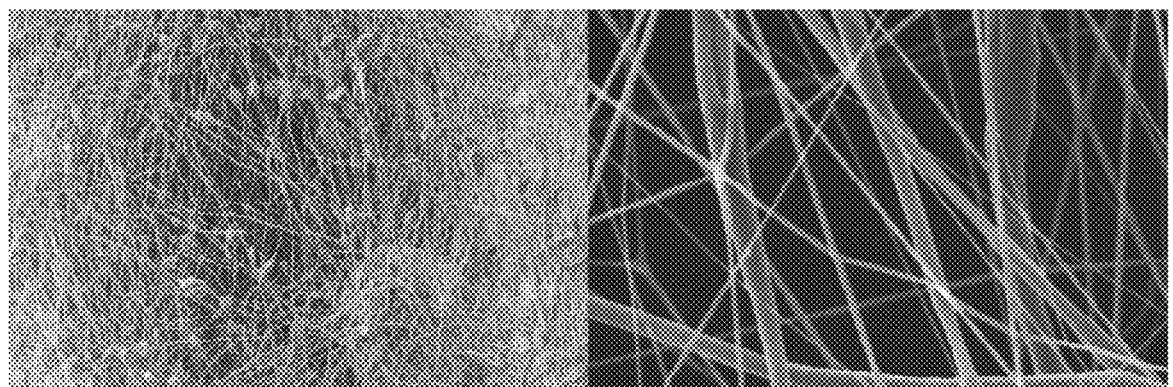
FIG. 15 is a set of SEM images showing the morphological analysis of electrospun fibers having a thickness of 254.84 μm (top row) or 308.94 μm (bottom row) at varying degrees of zoom.
Figure 15:
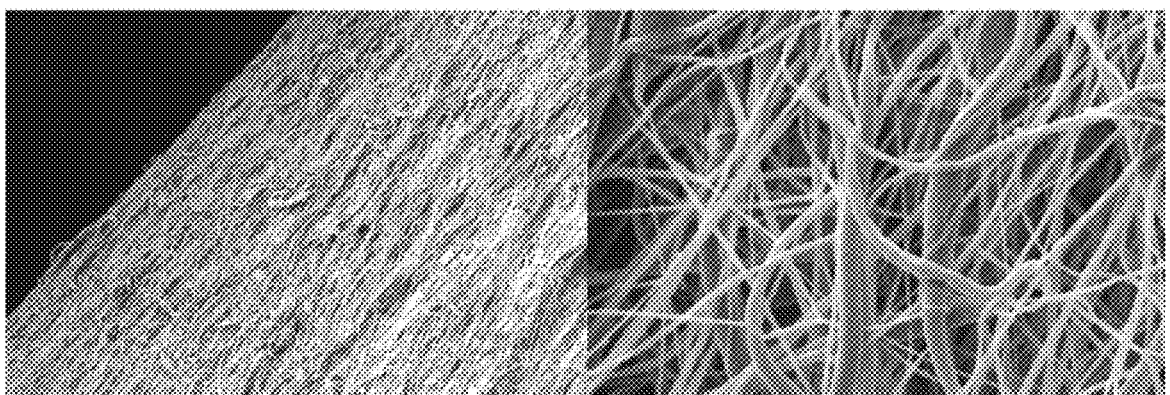
Figure 16A:
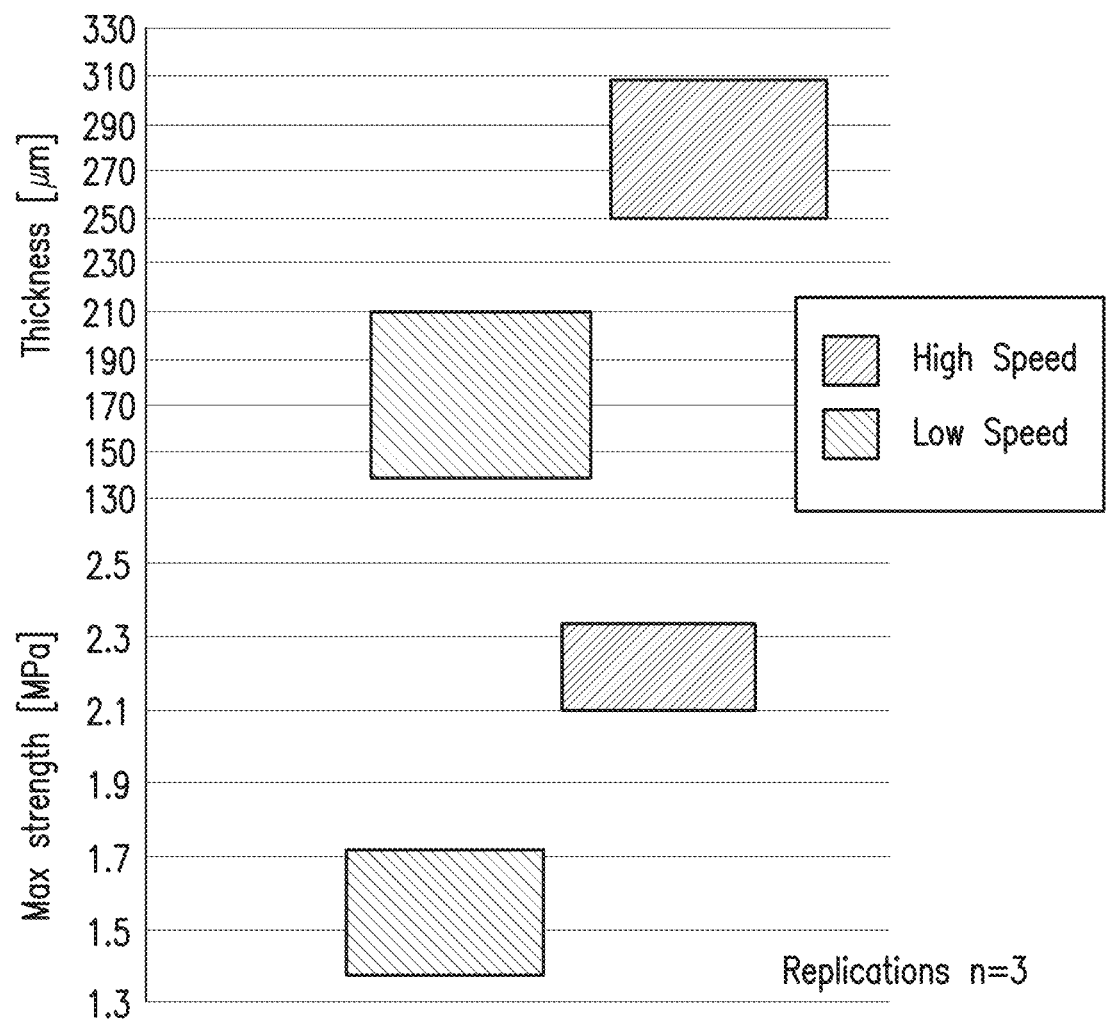
FIGS. 16A and 16B show physical and mechanical properties of membranes.
Figure 16B:
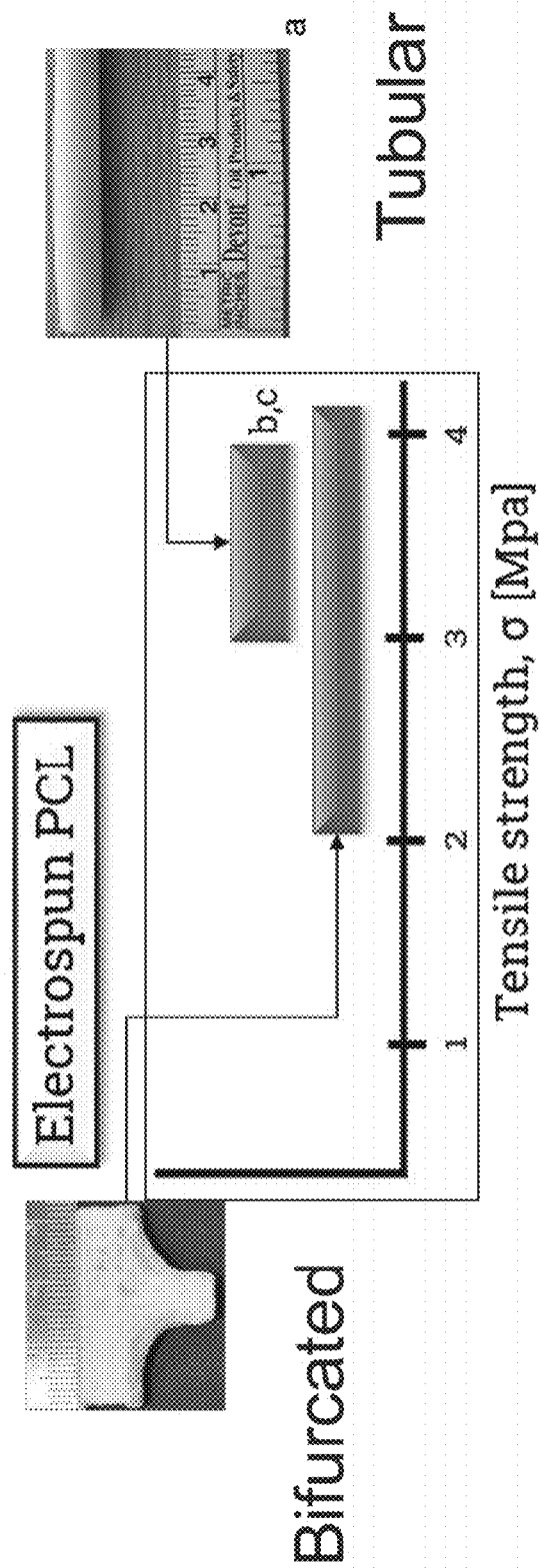

Different mandrel and scaffold materials and process parameters can be tested, and more realistic shapes for the mandrel can be considered (as shown in FIGS. 11A and 11B).

A combination of directed electrical field and dynamic positioning of the mandrel is disclosed herein to generate resorbable scaffolds with bifurcated tubular shapes. The approach produced a mat of electrospun fibers on top of a bifurcated tubular mandrel. Mechanical testing of the bifurcated scaffolds is reported, with maximum indentation force between 0.7 and 2.3 N. In tension tests, the scaffolds showed an average maximum strength of 1.21 MPa (no indexing condition) and 2.174 MPa (indexing in the B direction).

Example 2

This example describes an electrospun bifurcated tubular scaffolds (EBTS) built by combining electrospinning and a dynamic positioning mechanism. The EBTS were made of polycaprolactone (PCL) using low and high-speed profiles for the positioning mechanism. Mechanical characterization was carried out in order to evaluate the EBTSs. Indentation tests of the bifurcated grafts showed an indentation force between 2.92 N (low-speed) and 4.29 N (high speed). Tension tests showed an average strength of 1.38 MPa with low speed profile and 2.34 Mpa with high speed profile.

The increase of rotational and translational speeds of the dynamic mechanism improves the electrospun fibers distribution and enhance EBTS mechanical strength. Environmental conditions for the experiments impacted EBTS material properties. Changes in room temperature and humidity can affect the viscosity of the PCL solution. Lower temperature and humidity can reduce the density of distribution of the electrospun fibers and cause a reduction of mechanical properties.

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A method of making a branching graft, the method comprising:
    providing a continuous, branched mandrel, wherein the branched mandrel comprises a first mandrel tubular shape that defines a first mandrel lumen extending along a first mandrel axis, and a second mandrel tube that defines a second mandrel lumen extending along a second mandrel axis, wherein the first mandrel axis creates an angle with the second mandrel axis,
    providing an electrically conductive internal electrical field collector comprising a first collector end, a second collector end, a collector outer surface located between both collector ends, a collector longitudinal axis extending through the first collector end and the second collector end, and at least one articulating feature positioned between the first collector end and the second collector end,
    positioning the branched mandrel on the internal electrical field collector such that the internal electrical field collector extends through the first mandrel lumen, wherein the branched mandrel is positioned on a portion of the elongated internal electrical field collector such that the branched mandrel does not encompass the at least one articulating feature,
    bending the internal electrical field collector away from a longitudinal axis extending through the first end of the electrical field collector and the second end of the electrical field collector, thereby rotating the branched mandrel about the first mandrel axis and the second mandrel axis, coating the branched mandrel in densely tangled fibers while rotating the internal electrical field collector about the longitudinal axis, thereby forming a branching graft around the branched mandrel, and removing the branched mandrel and the branching graft from the internal electrical field collector.

2. The method of claim 1, wherein bending the internal electrical field collector comprises activating the at least one articulating feature on the internal electrical field collector.

3. The method of claim 2, wherein bending the internal electrical field collector comprises compressing or stretching the internal electrical field collector along the longitudinal axis, the first mandrel axis, or the second mandrel axis.

4. The method of claim 3, wherein the length of the internal electrical field collector changes along the longitudinal axis, the first mandrel axis, or the second mandrel axis.

5. The method of claim 2, wherein bending the internal electrical field collector comprises translating the internal electrical field collector along a transverse axis extending perpendicular to the longitudinal axis.

6. The method of claim 5, wherein the length of the internal electrical field collector changes along the transverse axis.

7. The method of claim 2, wherein bending the internal electrical field collector comprises compressing or stretching the internal electrical field collector along a longitudinal axis and translating the internal electrical field collector along a transverse axis.

8. The method of claim 1, wherein coating the mandrel in densely tangled to fully organized weave of fibers further comprises depositing the fibers by an electrospinning process.

9. The method of claim 8, wherein the first mandrel axis and the second mandrel axis meet at a reference point, and wherein the method further comprises aligning the origin of an electrospinning nozzle to the reference point.

10. The method of claim 1, wherein the method further comprises 3D printing the branched mandrel prior to positioning the branched mandrel on an elongated internal electrical field collector.

11. The method of claim 1, wherein the method further comprises removing the branched mandrel from the formed branching graft.

12. The method of claim 1, wherein the branching graft comprises a tubular tract.

13. The method of claim 12, wherein said tubular tract comprises the digestive tract, oropharyngeal tract, nasal tract, reproductive tracts, ventricular tracts, valvular structures along tubular tracts, vascular structures within and outside organs, tubular structures in other organs that include nervous, body humor transmitting or filtering, structural, or sensory tissues.

14. The method of claim 12, wherein the branching graft comprises a machine tubular structure for engine, heating, cooling, hydraulic, or other mechanical devices.

\* \* \* \* \*